United States Patent [19]
Pflugfelder et al.

[11] Patent Number: 5,652,209
[45] Date of Patent: Jul. 29, 1997

[54] USE OF SECRETORY PRODUCTS OF HUMAN LACRIMAL GLAND ACINAR EPITHELIA FOR TEAR REPLACEMENT THERAPY

[75] Inventors: Stephen C. Pflugfelder; Kenichi Yoshino; Scheffer C. G. Tseng; Andrew J. W. Huang, all of Miami, Fla.

[73] Assignee: University of Miami, Miami, Fla.

[21] Appl. No.: 235,673

[22] Filed: Apr. 29, 1994

[51] Int. Cl.⁶ .................................................. A61K 38/18
[52] U.S. Cl. ............................... 514/2; 514/12; 514/13; 514/912
[58] Field of Search .................. 514/2, 12, 912

[56] References Cited

U.S. PATENT DOCUMENTS

| | | |
|---|---|---|
| 4,745,100 | 5/1988 | Gilbard et al. . |
| 5,023,090 | 6/1991 | Levin . |
| 5,064,655 | 11/1991 | Uster et al. . |
| 5,212,162 | 5/1993 | Missel et al. . |

FOREIGN PATENT DOCUMENTS

WO94/01121  1/1994  WIPO .

OTHER PUBLICATIONS

Kenichi Yoshino, Scheffer C.G. Tseng, Stephen C. Pugfelder, The Characterization of Human Lacrimal Gland Acinar and Ductal Epithelia in Various Culture Systems, Proceedings of the Fourth International Symposium, Tokyo, Japan, Aug. 11–13, 1993, M. Homma, S. Sugai, T. Tojo, N. Miyasaka, M. Akizuki, edtiros, pp. 1–4.

Steven E. Wilson, Scott A. Lloyd, Robert H. Kennedy, Basic Fibroblast Growth Factor (FGFb) and Epidermal Growth Factor (EGF) Receptor Messenger RNA Production in Human Lacrimal Gland, Investigative Opthalmology & Visual Science, vol. 32, No. 10, Sep. 1991, pp. 2816–2820.
Sjogren's Syndrome Foundation, Inc. Newsletter, Mar. 1994—Cytokine Profiles in SS and Guides to New Therapy, Noriyoshi Ogawa, MD, PhD.
Z. Ji, K. Yoshino, D. Monroy, S.C. Pflugfelder, Transforming Growth Factor β (TGFβ) Expression in the Human Lacrimal Gland, Investigative Ophthalmology & Visual Science, Mar. 15, 1994, vol. 35, No. 4, p. 1792.
A. Gupta, K. Yoshino, S.C. Pflugfelder, The Identification of Transforming Growth Factor Beta–A in Carbachol–Stimulated Cultured Lacrimal Gland Acinar Cell Supernatant and Human Tears Using Sandwich Elisa Techniques, 1990 ARBO Abstract Form. Abstract to be Published in Investigative Ophthalmology & Visual Science, Mar. 15, 1994, vol. 35, No. 4, p. 1792.
K. Yoshino, A. Gupta, S.C.G. Tseng and S.C. Pflugfelder, Tear Protein Synthesis and diGA Uptake in Human Lacrimal Gland Acinar Culture, Investigative Ophthamology & Visual Science, Mar. 15, 1994, vol. 35, No. 4, p. 1792.
Chemical Abstract 120 : 124917 (1991), Glaser et al.

*Primary Examiner*—Zohreh Fay
*Attorney, Agent, or Firm*—Cushman Darby & Cushman Intellectual Property Group of Pillsbury Madison & Sutro, LLP

[57] ABSTRACT

The present invention relates to medicinal compositions and more particularly refers to such compositions for tear replacement therapy having products of human lacrimal gland acinar epithelia, and more specifically, growth factors or cytokines, in particular, the transforming growth factor beta (TGFβ).

4 Claims, 10 Drawing Sheets

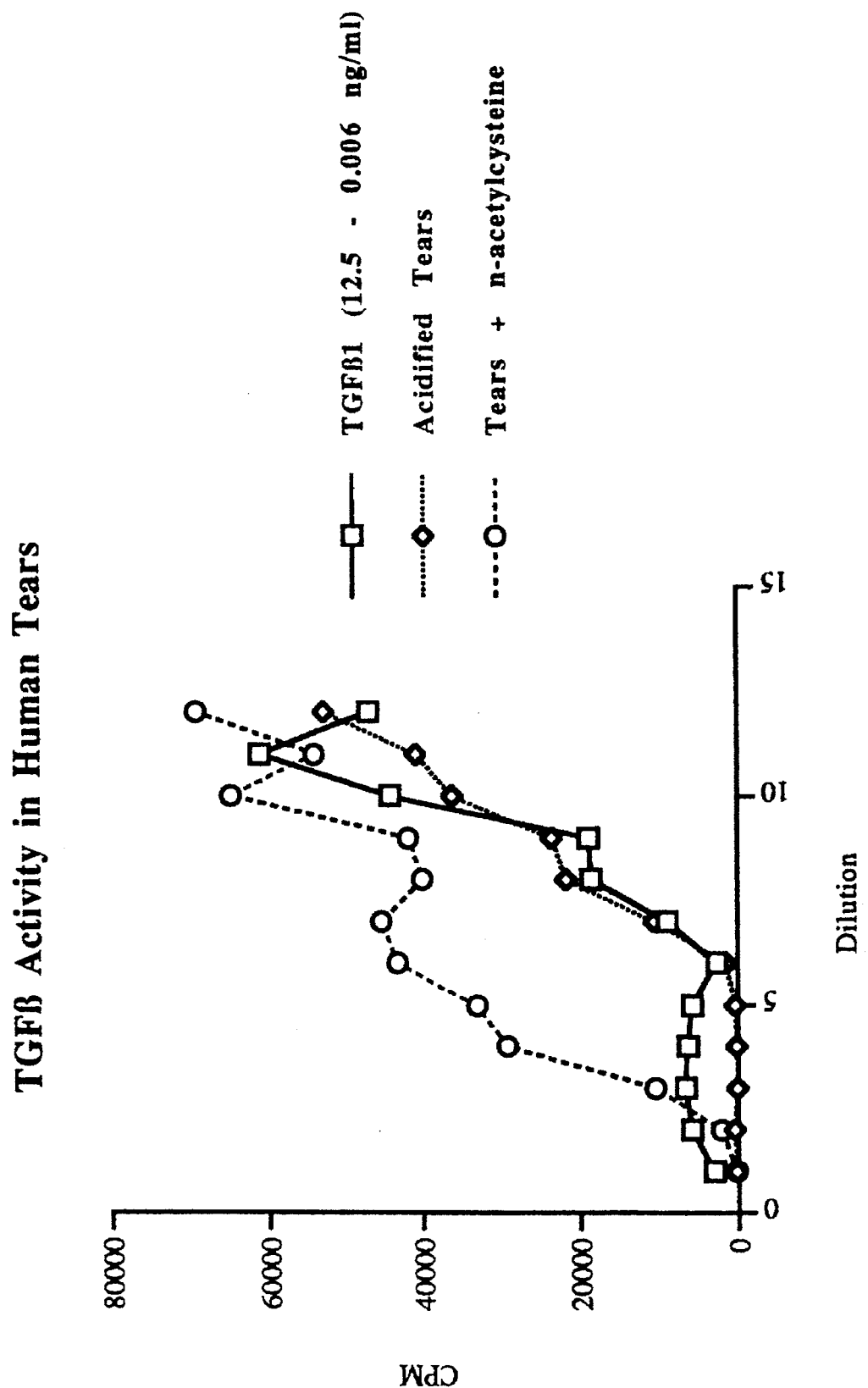

Immunoblot of human tears for TGF-β

USE OF SECRETORY PRODUCTS OF HUMAN LACRIMAL GLAND ACINAR EPITHELIA FOR TEAR REPLACEMENT THERAPY

BACKGROUND OF THE INVENTION

1. Field of the Invention

The present invention relates to medicinal compositions and more particularly refers to such compositions for tear replacement therapy having products of human lacrimal gland acinar epithelia, and more specifically, growth factors or cytokines, in particular, the transforming growth factor beta (TGFβ).

2. Background Information

Aqueous tear deficiency is a common condition that in its most severe form may be associated with disabling ocular irritation, and visual morbidity due to corneal epitheliopathy and/or ulceration. The conjunctival pathology of Sjogren's Syndrome (SS), the most severe type of aqueous tear deficiency, consists of abnormal terminal differentiation with significantly reduced bulbar goblet cell densities (Pflugfelder, S. C. et al. Ophthalmology 1990;97:985–991), decreased expression of mucins by the superficial epithelium (Table I)(Pflugfelder, S. C. et al. 1994 ARVO abstracts. Invest. Ophthalmol. Vis. Sci. 1994; 34: 1692)), and aberrant expression of immune activation markers (HLA Class II antigens and ICAM I) and interleukin 6 (IL-6) (Jones, D. T. et al. Invest. Ophthalmol. Vis. Sci. (in press)).

Although this may be due in part to mechanical trauma related to the reduced preocular tear film, it may also represent abnormal terminal differentiation due to lack of biologically active tear constituents. At the present time, epidermal growth factor (EGF) is the only cytokine that has been detected in human tears (van Seten, G. B. et al. Graeffe's Arch. Clin. Exp. Ophthalmol. 1989;227: 184–187). Reduced tear EGF concentrations have been reported in one patient with aqueous tear deficiency (van Seten, G. B. et al. Curr. Eye Res. 1991; 10:523–527; however, the biologic activity of tear EGF has not been evaluated.

Tear secretion by the human lacrimal gland is influenced by neurotransmitters and hormones (Dartt, D. Curr. Eye Res. 1989;8:619–636; Sullivan, D. A. *The Neuro Endocrine-immune Network* S. Freier, Editor. Boca Raton, Fla. 1990 CRC Press, pp 199–238). Jordan and Baum have reported that the majority of tear secretion is reflexive, resulting from sensory stimulation of the lids and ocular surface (Jordan, A. and Baum, J. Ophthalmology 1980;87:920–930). A marked reduction in neural-stimulated tear secretion is an early clinical sign in Sjogren's Syndrome (Tsubota, K. Am. J. Ophthalmol. 1991; 111: 106–108), but the clinical consequences of reduced neural-stimulated tears have not been established.

We recently discovered that the pathologic changes associated with Sjogren's Syndrome may be due in part to reduced concentrations of cytokines produced by the lacrimal gland and secreted into the tears that are essential for

TABLE I

Results of Immunohistochemical Staining of Bulbar Conjunctival Epithelial Cells on Impression Cytology Specimens using Mucin-Specific Antibody L6

| Group | Temporal Conjuctiva (% +) | Inferior Conjunctiva (% +) |
|---|---|---|
| Sjogren Syndrome (SS) ATD | 18.2 | 18.2 |
| Non Sjogren Syndrome ATD | 66.7 | 88.9 |
| inflammatory MGD | 77.8 | 88.9 |
| Atrophic MGD | 77.8 | 100 |
| Control | 100 | 100 |
| | SS vs Inflam. MGD p = 0.022 | SS vs non SS ATD p = 0.005 |
| | SS vs Atrophic MGD p = 0.022 | SS vs Inflam. MGD p = 0.005 |
| | SS vs control p = 0.001 | SS vs Atrophic MGD p = 0.001 |
| | | SS vs control p = 0.001 |

ATD = aqueous tear deficiency, MGD = meibomian gland disease

At the present time, biological activity of tears on the health and differentiation of the ocular surface epithelia has not been evaluated. Clinical signs and ocular surface pathologic changes in patients with aqueous tear deficiency suggest that the tears may have more than a lubricating role for the ocular surface. One of the most specific clinical signs of severe aqueous tear deficiency is staining of the conjunctival and/or cornea with the diagnostic dye rose-bengal. Recently reported experimental evidence suggests that rose-bengal staining of the ocular surface epithelia may result from lack of cell coating by normal tear constituents, predominantly tear mucins (Feenstra, R. P. and Tseng, S. C. G. Arch. Ophthalmol. 1992;110:984–993). Mucin-producing goblet cells and production of cell-membrane associated mucins by the superficial stratified epithelia are markers of terminal differentiation in the normal human conjunctiva. A marked reduction in expression of both types of conjunctival mucin has been detected in the conjunctival epithelia of Sjogren's Syndrome patients (Pflugfelder, S. C. et al. Ophthalmology 1990;97:985–991. Pflugfelder, S. C. et al., 1994 ARVO abstracts Invest. Ophthalmol. Vis. Sci. 1994; 34: 1692).

normal health and differentiation of the ocular surface epithelia. Based on its ability to induce differentiation of intestinal mucosa (Kurokowa, M. et al., Biochem. Biophys. Comm. 1987; 142:775–782), and corneal epithelia (Kruse, F. E. and Tseng. S. C. G. Invest. Ophthalmol. Vis. Sci. 1993;34: 1963–1976), and its ability to down regulate HLA Class II antigen and IL-6 expression (Lucas, C. et al. Ciba Foundation 1991; 157:98–114), we hypothesized that transforming growth factor beta (TGFβ) may be one of the biologically essential tear cytokines. Recently, TGF has been reported to be produced by mammary gland acini (Maier, R. et al. Mol. Cell. Endocrinol. 1991;82: 192–198) and secreted into milk.

TGFβ is a multi-functional biologically essential cytokine. TGFβ has a spectrum of biologic activity and has been reported to induce differentiation and inhibit proliferation of mucosal epithelia, including rabbit corneal epithelia (Kurokowa, M. et al. Biochem. Biophys. Comm. 1987; 142:775–782; Kruse, F. E. and Tseng. S. C. G. Invest. Ophthalmol. Vis. Sci. 1993;34: 1963–1976). TGFβ has also been reported to stimulate synthesis of extra cellular matrix components and has been shown to induce these effects on corneal stromal fibroblasts (Ohji, M. et al. Curr. Eye. Res. 1993;12:703–709). Finally, TGFβ has immunosuppressive activity that includes inhibition of T-cell proliferation, down regulation of expression of inflammatory cytokines such as IL-6 and immune activation markers such as HLA class II antigens (Lucas, C. et al. Ciba Foundation 1991; 157:98–114).

At the present time, commercially available artificial tear replacements are composed of synthetic polymers, buffers, and electrolytes in an aqueous solution. Examples of such solutions include "BION" (Alcon Laboratories, Fort Worth, Tex.) and "REFRESH PLUS" (Allersan, Irvine, Calif.). Major components of commercially available artificial tear replacement solutions, Ophthalmic lubricants which protect the eye from drying, and ocular decongestants, are listed in TABLES II, III, and IV, respectively. These solutions contain no biologically active components to modulate the health and differentiation of ocular surface epithelia. Tear replacement therapies containing biologically active components could potentially reverse pathologic ocular surface epithelial changes, and would present a great advance in treatment of severe aqueous tear deficiency states.

TABLE III-continued

OPHTHALMIC LUBRICANTS

| TRADE NAME | COMPOSITION |
| --- | --- |
| Duolube (Bausch & Lomb) | Sterile ointment containing white petrolatum and mineral oil. |
| Duratears Naturale (Alcon) | Sterile ointment containing white petrolatum, liquid lanolin, and mineral oil. |
| HypoTears (Iolab) | Sterile ointment containing white petrolatum and light mineral oil. |
| Lacri-Lube S.O.P. (Allergan) | Sterile ointment containing 42.5% mineral oil, 55% white petrolatum, lanolin alcohol, and chlorobutanol. |
| Refresh P.M. (Allergan) | Sterile ointment containing 41.5% mineral oil, 55% white petrolatum, petrolatum, and lanolin alcohol. |

TABLE II

ARTIFICIAL TEAR PREPARATIONS

| MAJOR COMPONENT | CONCENTRATION | TRADENAME | PRESERVATIVE/EDTA |
| --- | --- | --- | --- |
| Carboxy methycellulose | 0.5% | Cellufresh | None |
|  | 1% | Celluvisc | None |
| Hydroxyethyl cellulose |  | Lyteers | Benzalkonium Cl + EDTA |
|  |  | TearGard | Sorbic Acid + EDTA |
| Hydroxyethyl cellulose + Polyvinyl Alcohol |  | Neo-Tears | Thimerosal + EDTA |
| Pydroxyethyl cellulose + Povidone |  | Adsorbotear | Thimerosal + EDTA |
| Hydroxypropyl Cellulose |  | Lacrisert (Biodegradable insert) | None |
| Hydroxypropyl Methylcellulose | 0.5% | Isopto Plain | Benzalkonium Cl |
|  |  | Isopto Tears | Benzalkonium Cl |
|  |  | Tearisol | Benzalkonium Cl + EDTA |
|  | 1% | Isopto Alkaline | Benzalkonium Cl |
|  |  | Ultra Tears | Benzalkonium Cl |
| Hydroxypropyl Methylcellulose + Dextran 70 |  | Tears Naturale | Benzalkonium Cl + EDTA |
|  |  | Tears Naturale II | Polyquad |
|  |  | Tears Naturale Free | None |
| Hydroxypropyl Methylcellulose + Gelatin A |  | Lacril | Chlorobutanol + Polysorbate 80 |
| Methylcellulos | 1% | Murocel | Methyl- + Propylparabens |
| Polyvinyl Alcohol | 1.4% | Akwa Tears | Benzalkonium Cl + EDTA |
|  |  | Just Tears | Benzalkonium Cl + EDTA |
|  |  | Liquifilm Tears | Chlorobutanol |
|  | 3% | Liquifilm Forte | Thimerosal + EDTA |
| Polyvinyl Alcohol + PEG-400 + Dextose | 1% | Hypotears | Benzalkonium Cl + EDTA |
|  |  | Hypotears PF | EDTA |
| Polyvinyl Alcohol + Povidone | 1.4% | Murine | Benzalkonium Cl + EDTA |
|  | 0.6% | Refresh | None |
|  |  | Tears Plus | Chlorobutanol |

TABLE III

OPHTHALMIC LUBRICANTS

| TRADE NAME | COMPOSITION |
| --- | --- |
| AKWA Tears Ointment (Akorn) | Sterile ointment containing white petrolatum, liquid lanolin, and mineral oil. |

TABLE IV

| DRUG | TRADE NAME | ADDITIONAL COMPONENTS |
|---|---|---|
| OCULAR DECONGESTANTS | | |
| Naphazoline Hydrochloride | AK-Con* | Benzalkonium Cl + edetate disodium |
| | Albalon* | Benzalkonium Cl + edetate disodium |
| | Clear Eyes | Benzalkonium Cl + edetate disodium |
| | Degest 2 | Benzalkonium Cl + edetate disodium |
| | Naphcon* | Benzalkonium Cl + edetate disodium |
| | Opcon* | Benzalkonium Cl + edetate disodium |
| | Vasoclear | Benzalkonium Cl + edetate disodium |
| | Vasocon Regular* | Phenylmercuric acetate |
| Phenylephrine Hydrochloride | AK-Nefrin | Benzalkonium Cl + edetate disodium |
| | Efricel | Benzalkonium Cl + edetate disodium |
| | Eye Cool | Thimerosal + edetate disodium |
| | Isopto Frin | Benzalkonium Cl + edetate disodium |
| | Prefin Liquifilm | Benzalkonium Cl + edetate disodium |
| | Relief | — |
| | Tear-Efrin | Benzalkonium Cl + edetate disodium |
| | Velva-Kleen | Thimerosal + edetate disodium |
| Tetrahydrozoline Hydrochloride | Collyrium | Benzalkonium Cl + edetate disodium |
| | Murine Plus | Benzalkonium Cl + edetate disodium |
| | Soothe* | Benzalkonium Cl + edetate disodium |
| | Tetracon | Benzalkonium Cl + edetate disodium |
| | Visine | Benzalkonium Cl + edetate disodium |
| DECONGESTANT/ASTRINGENT COMBINATIONS | | |
| Naphazoline Hydrochloride plus Zinc Sulfate | Clear Eyes ACR (Allergy/Cold Relief) | Benzalkonium Cl + edetate disodium |
| Phenylephrine Hydrochloride plus Zinc Sulfate | Prefrin-Z Zincfrin | Thimerosal Benzalkonium Cl |
| Tetrahydrozoline plus Zinc Sulfate | Visine A.C. | Benzalkonium Cl + edetate disodium |

*Prescription medication

SUMMARY OF THE INVENTION

We have recently been able to culture human lacrimal gland acinar epithelia which secrete proteins typically produced by lacrimal gland secretory acini in vivo (Yoshino, K. et al., Proceedings of the Fourth International Symposium on Sjorgren's Syndrome (1993), p. 804). In addition, we have evaluated human tears for TGFβ using the CCL-64 mink lung epithelial cell (MLEC) growth inhibition assay and sELISA. Results indicate that human lacrimal gland acini produce and secrete TGFβ into the tears, and that there are factors in human tears capable of binding TGFβ.

It is therefore an object of the present invention to provide cultured human lacrimal gland acinar epithelia as a model of in vivo secretory acinar function. These cultures can be used for testing of agents which stimulate or inhibit tear secretion and the analysis of biologically active tear constituents that are secreted by the lacrimal gland which can be used for the treatment of diseases affecting the ocular epithelia. Specifically, diseases of the ocular surface associated with aqueous tear deficiency.

It is another object of the present invention to provide a medicinal formulation suitable for the treatment of various conditions which result in tear deficiency or ocular irritation. Conditions benefiting from physiologic tear replacement include patients with lacrimal gland dysfunction, destruction or surgical removal (Sjogren's Syndrome, post radiation, altered innervation, surgical removal for treatment of tumor).

It is yet another object of the invention to provide tear replacement compositions containing TGFβ which are more effective than the composition presently in use which do not contain biologically active components. According to the present invention, tear replacement compositions are provided by adding TGFβ to a pharmaceutical composition for application to the eye in order to lubricate the eye or to supplement tears.

According to the present invention, tear replacement compositions as stated above may also contain any or other components produced by lacrimal gland epithelia, naturally present in human tears such as antimicrobial proteins (for example lactoferrin and lysozyme), retinol binding protein (for example tear specific pre-albumin), biologically active components or cytokines such as epidermal growth factor, or retinol.

Compositions according to the present invention can be used to treat aqueous tear deficiency and conditions associated with alterations of the ocular suface epithelia including hyperproliferation, squamous metaplasia, loss of goblet cells, and abnormal terminal differentiation among other ocular surface pathologic changes that lead to ocular irritation.

The foregoing and other objects, advantages and characterizing features of this invention will become apparent from the following description of certain illustrative embodiments of the invention.

DETAILED DESCRIPTION OF THE INVENTION

Figures 1, 1A:
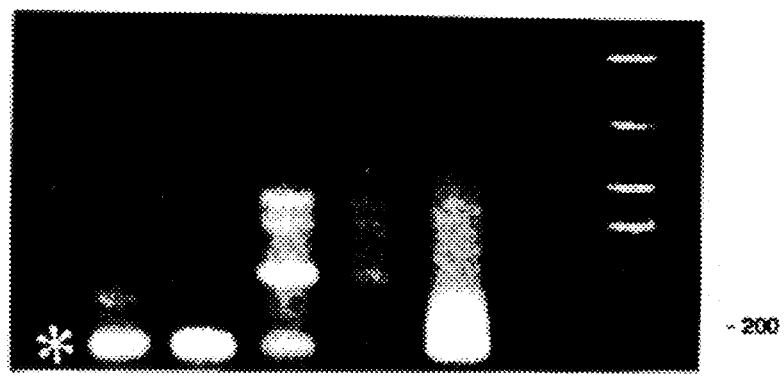
FIG. 1A. Expression of TGFβ1 mRNA in normal human lacrimal gland biopsies and cultured human lacrimal gland acinar epithelia. PCR products of the appropriate size (161 bp) from amplification of cDNA prepared from human lacrimal gland epithelial cultures (lane 1) and human lacrimal gland biopsies (lane 2-4) with TGF-β1 specific primers were noted on an ethidium bromide stained agarose gel (upper figure) and Southern hybridization (bottom figure). Lane 5 contains TGF-β1 cDNA. Lane 6—blank, Lane 7—molecular weight standards.
Figures 1, 1A, 2:
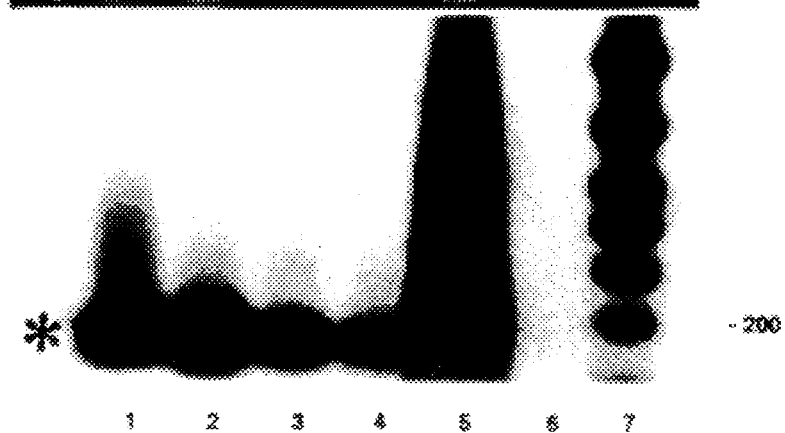

In accordance with the present invention, tear replacement compositions containing TGFβ, where TGFβ is either TGF-β1 or TGF-β2 or a combination thereof, by way of non limiting illustration, be applied to the eye in animals and humans as a drop or within ointments, gels, liposomes, or biocompatible polymer discs or pellet. They can be attached to, carried by and/or contained within contact lenses that are placed on the eye. In general, it is desired that the mode of application be such that the composition enters the tear film or otherwise makes contact with the surface of the eye.

Further in accordance with the invention, a replacement tear composition is made by combining TGFβ with a physiologically acceptable carrier. Preferably, the preparation will be unit dose, refrigerated, with or without preservative. The composition may also contain a physiologically compatible ophthalmic vehicle as those skilled in the art can select using conventional criteria. The vehicles may be selected from the known ophthalmic vehicles which include but are not limited to water, polyethers such as polyethylene glycol 400, polyvinyls such as polyvinyl alcohol, povidone, cellulose derivatives such as carboxy methylcellulose, methylcellulose and hydroxypropyl methylcellulose, petroleum derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium hyaluronate and salts such as sodium chloride and potassium chloride, calcium chloride, magnesium chloride, zinc chloride, and buffer such as sodium bicarbonate or sodium lactate. High molecular weight molecules can also be used, such as mucins.

Preferred preservatives are physiologically compatible and do not inactivate TGFβ or other peptides or cytokines present in the composition. Preservatives include but are not limited to alcohols such as chlorobutanol, and benzalknonium Cl and EDTA, though other appropriate preservatives known to those skilled in the art may be used.

In a preferred embodiment, the concentration of TGFβ in the tear solution is from 250 pg/ml to 12.5 ng/ml, preferably 200 pg/ml to 12.0 ng/ml. Active TGFβ concentrations in human tears range from 250 pg/ml to 12.5 ng/ml (mean 3.83 ng/ml). There appears to be a total latent TGFβ concentration of approximately 30 ng/ml in tears. Ideally, therapeutic TGFβ should be administered bound to its natural carrier or binding protein(s) in tears. At the present time, these appear to be mucins because immunoreactivity of TGFβ in native tears is at a high molecular weight (approximately 1000 kD), the molecular weight of tear mucins. Data suggests that most TGFβ in tears is in the proform (approximately 110 kD). Typically, this proform is converted to the active from by proteolytic enzymes such as plasmin. Plasminogen activator is normally found in human tears. It is likely that concentrations of this protein are reduced in patients with aqueous tear deficiency. Therefore, it may be necessary to use purified (lyophilized) active TGFβ. The source of this cytokine is not essential. It could be purified from platelets (a rich source of TGFβ1) or recombinant TGFβ could be used. Alternatively, cultured lacrimal gland acini could serve as the source of TGFβ. Other lacrimal gland produced tear constituents which may be desirable to add to physiologic tear replacements include, lactoferrin, 1–3 g/L (Kijlstra, A. et al. (1983), Br. J. Ophthalmol. 67:199–202), lysozyme, 0.5–4.5 g/L, and Tear specific pre-albumin, 0.5–1.5 g/L (Berman, E. R. Biochemistry of the Eye, Ed. C. Blakemore, Plenum Press, New York, 1991), mucins, and epidermal growth factor (EGF) 0.75–9.7 ng/ml (van Setten, G. B. et al. (1989) Graeffe's Arch. Clin. Exp. Ophthalmol. 22:184–187; Ohashi, Y. et al. (1989) Invest. Ophthalmol. Vis. Sci. 30:1879–1882), and Vitamin A, 16 ng/ml of retinol (Vitamin A is present in tears as retinol but would need to be added to tear replacement as trans retinoic acid) (Ubels, J. L. and Mac Rae, S. M. (1984) Current Eye Res. 3:815–822).

The following examples are presented to illustrate further various aspects of the present invention, but are not intended to limit the scope of the invention in any respect.

EXAMPLE 1

Production of TGFβ by Human Lacrimal Gland Epithelia

Figures 1, 1B:
FIG. 1B. Expression of TGFβ2 mRNA in normal human lacrimal gland biopsies and cultured human lacrimal gland acinar epithelia. A PCR product of approximately 450 bp was noted on an ethidium bromide stained agarose gel of amplification of cDNA prepared from human lacrimal gland epithelial cultures (lane 1) and human lacrimal gland biopsies (lanes 2–4) with TGF-β2 specific primers. On Southern hybridization, three hybridizations signals with approximate sized of 350-, 450-, and 500-bp were obtained from cDNA prepared from cultured lacrimal gland epithelia (lane 1) and one lacrimal gland biopsy (lane 2), while only two hybridization bands (350 and 450 bps) were obtained from cDNA prepared from the other two lacrimal gland biopsies (lanes 3 and 4). Multiple sized PCR products are most likely due to alternate splicing of the region of the TGF-β2 gene amplified with these primers. Lane 5 contains TGF-β2 cDNA. Lane 6—blank, Lane 7—molecular weight standards.
Figures 1, 1B, 2:
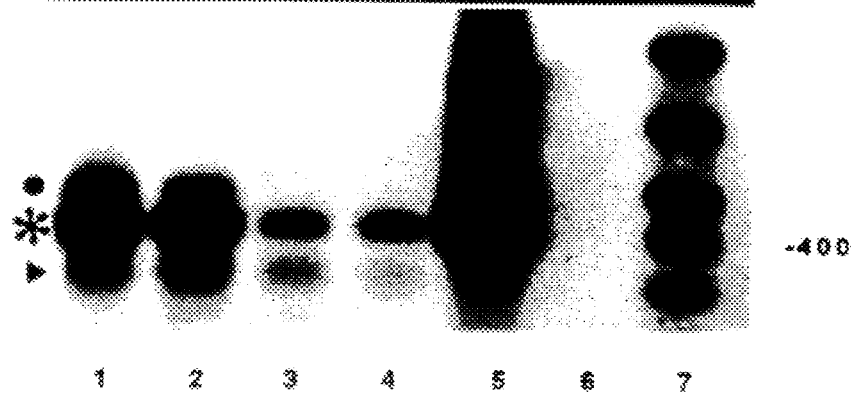
Figures 1, 2A:
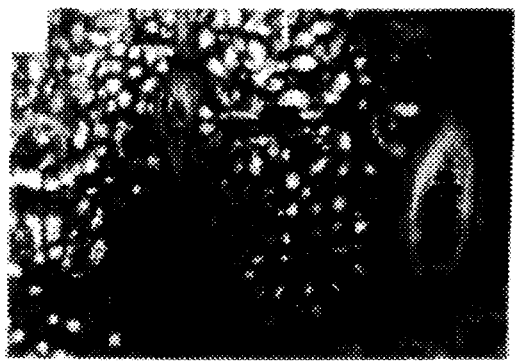
FIG. 2A. Expression of TGFβ1 and TGF2 protein in normal human lacrimal gland biopsies. (a) majority of tubuloacinar structures in all five human lacrimal gland biopsies showed immunoreactivity to a polyclonal antibody to all isotypes of TGF-β (pan TGF-β Ab, 40× original magnification). (b) Absence of immunoreactivity to TGF-β2-specific antisera was noted in all lacrimal gland biopsies (400× original magnification). (c) and (d). TGF-β1-specific antibodies produced strong immunoreactivity with epithelial cells in four or five lacrimal gland biopsies. The strongest staining with TGF-β1 antibodies was noted in the apical secretory portion and lumens of acinar epithelial complexes ((c)—100×, (d)—100× original magnification). (e) and (f). In sections where entire Tubuloacinar structures were visualized (asterisk), TGF-β1 staining appeared stronger in acinar than ductal epithelia ((e) imunofluorescent staining, (f)—phase, 100× original magnification).
Figures 2, 2A:
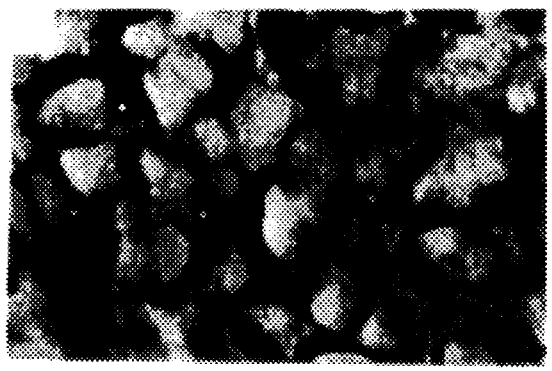
Figures 2, 2A, 3:
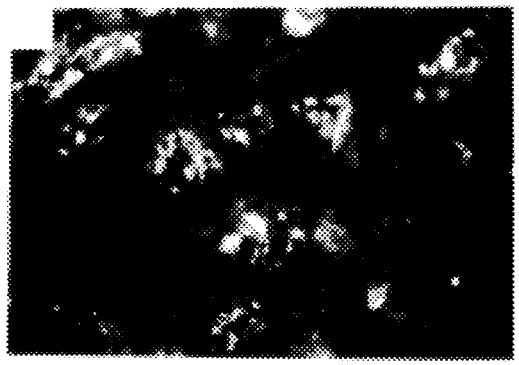
FIG. 3. Results of ELISA for TGF-β1 and TGF-β2 in supernatants (spnt) from human lacrimal gland acinar epithelial cultures and control media. TGF-β1 [] in culture supernatants were significantly greater than media or TGF-β2 (*0.169 ng/ml±0.021)in culture supernatants (P<0.05)
Figures 2, 2A, 3, 4:
FIG. 4. Growth inhibitory effects of native human tears in mink lung epithelial cell bioassay.
Figures 2, 2A, 3, 4, 5:
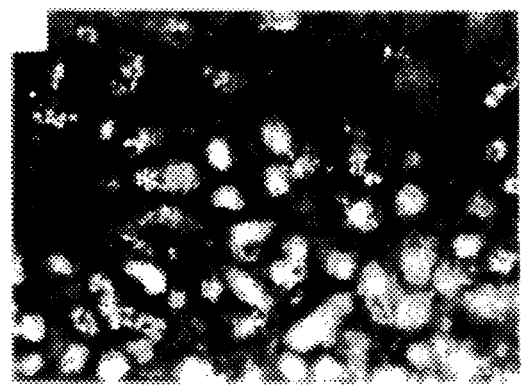
FIG. 5. Concentration of TGFβ in native tears treated with various physicochemical techniques.
Figures 2, 2A, 3, 4, 5, 6:
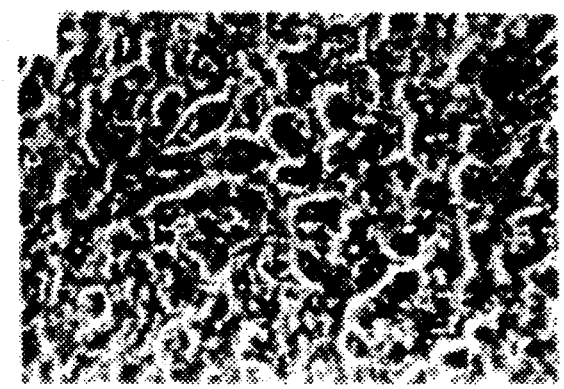
FIG. 6. Growth inhibitory effects of human tears following acidification or treatment with n-acetylcysteine ("MUCOSIL™", DEY Laboratories, Napa, Calif.) and heating.
Figures 1, 2B:
FIG. 2B. Expression of TGFβ1 and TGFβ2 protein in cultured human lacrimal gland acinar epithelia. The cytoplasm of cultured human lacrimal gland epithelia stained with both TGF-β1 (top figure) and TGF-β2 (bottom figure) antisera (100× original magnification).
Figures 2, 2B:
Figure 3:
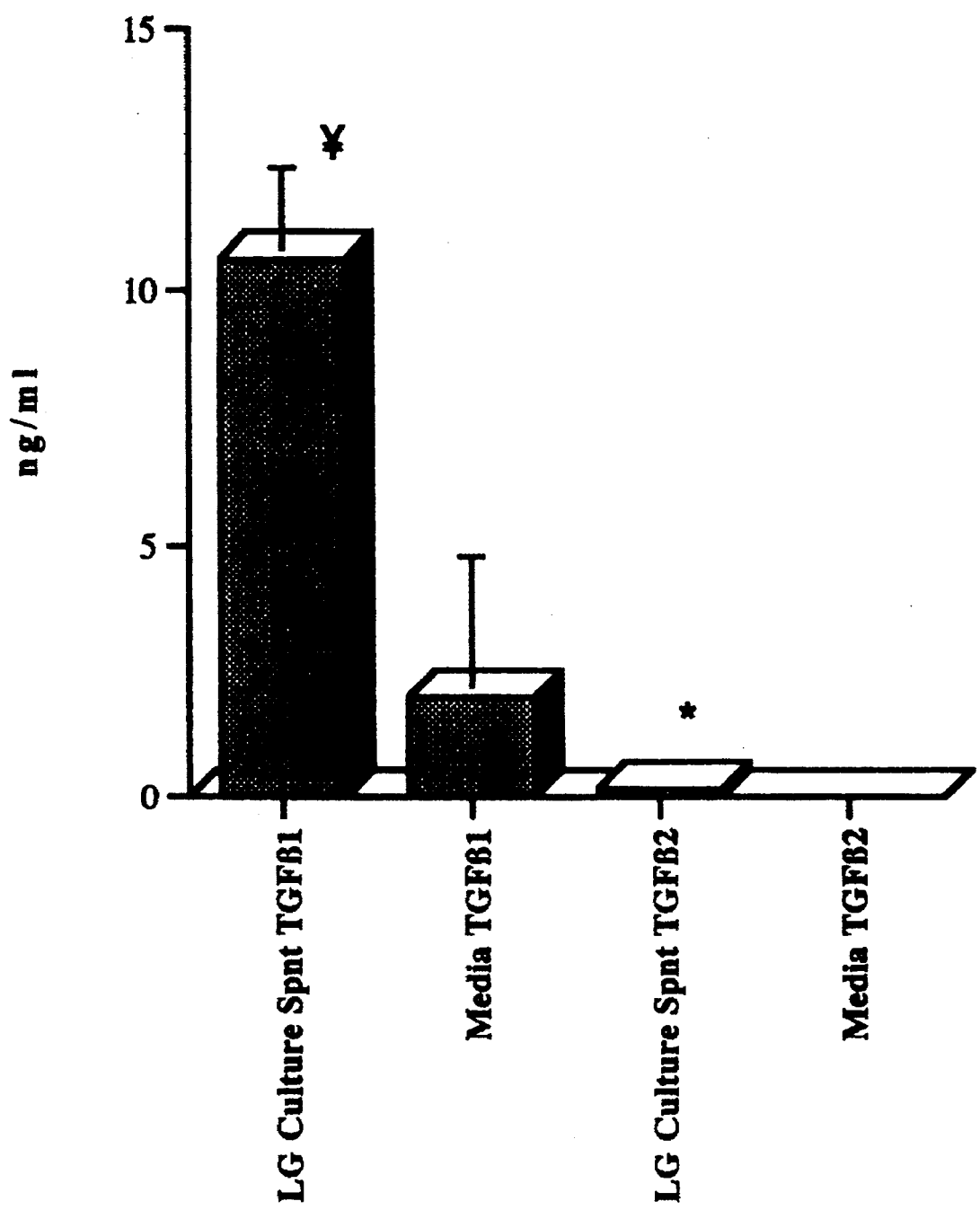
Figure 4:
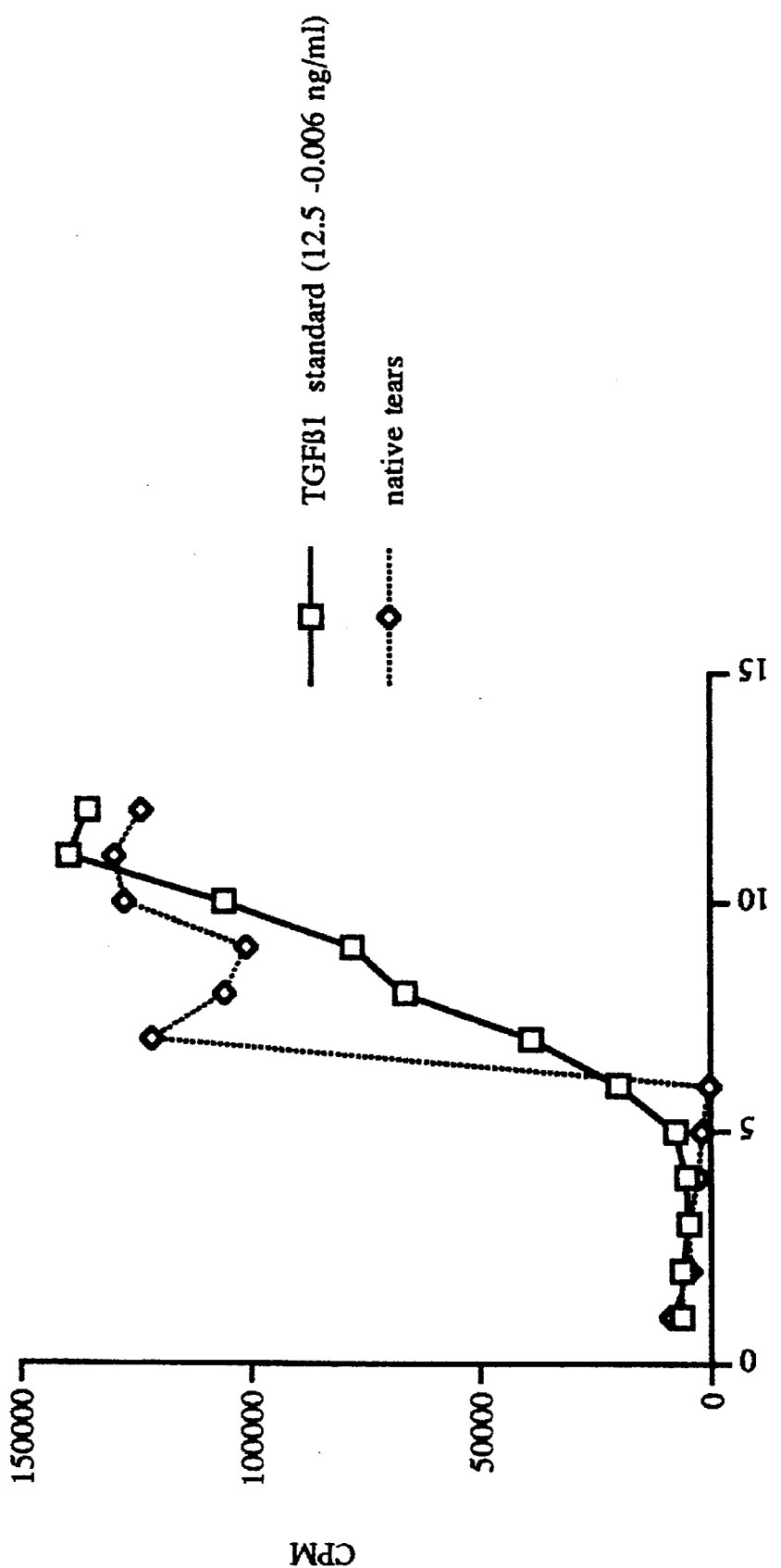
Figure 5:
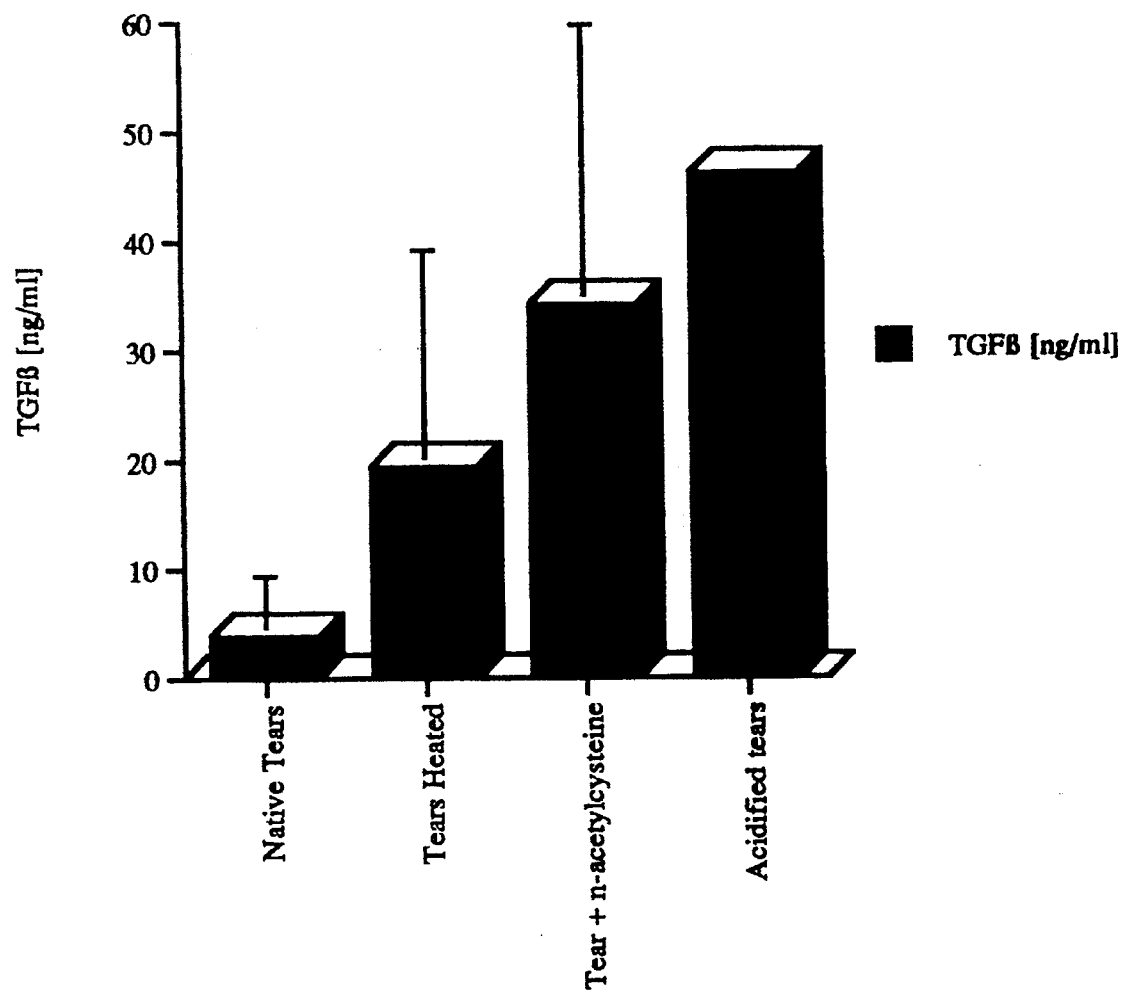

We have recently evaluated normal human lacrimal gland biopsies and cultured human lacrimal gland acinar epithelia (Yoshino, K. et al. Sjorgren's Syndrome—Proceedings of the Fourth International Symposium, 1993. Ed. M. Homma, S. Sugai, T. Tojo, N. Miyasajka and M. Akizuki, Kugler Publications, 1994, Amsterdam/New York) for expression of TGFβ1 and TGFβ2 mRNA and protein using RT-PCR, sELISA and immunohistochemisty, techniques known in the art (Ji, Z. et al. Invest. Ophthalmol. Vis. Sci. (1994 ARVO abstracts) 1994; 34: 1792). TGFβ1 and β2 mRNA expression was found in both lacrimal gland biopsies and acinar cultures (FIGS. 1A and 1B). In lacrimal gland biopsies, immunoreactivity to TGFβ1 but not TGF-β2 was detected in the secretory portion of the lacrimal gland acinar epithelia adjacent to the lumen by immunohistochemistry (FIG. 2A). The cytoplasm of cultured acinar epithelia showed immunoreactivity to both TGFβ1 and β2 specific antisera (FIG. 2B). TGFβ1 was detected in supernatants of lacrimal gland acinar cultures in significantly greater concentrations (0.5–2 ng/ml) than the control (culture media on substrate) by sandwich ELISA (sELISA, FIG. 3). Furthermore, stimulation of cultured human lacrimal gland acini with 0.01 mM carbachol (a cholinergic agonist) resulted in at least a 30% increase in TGFβ1 concentrations in the supernatants. These experiments indicate that TGFβ is produced and secreted by human lacrimal gland acinar epithelia, and that this secretion may be enhanced by cholinergic stimulation.

EXAMPLE 2

TGFβ in Human Tears

Figure 7:
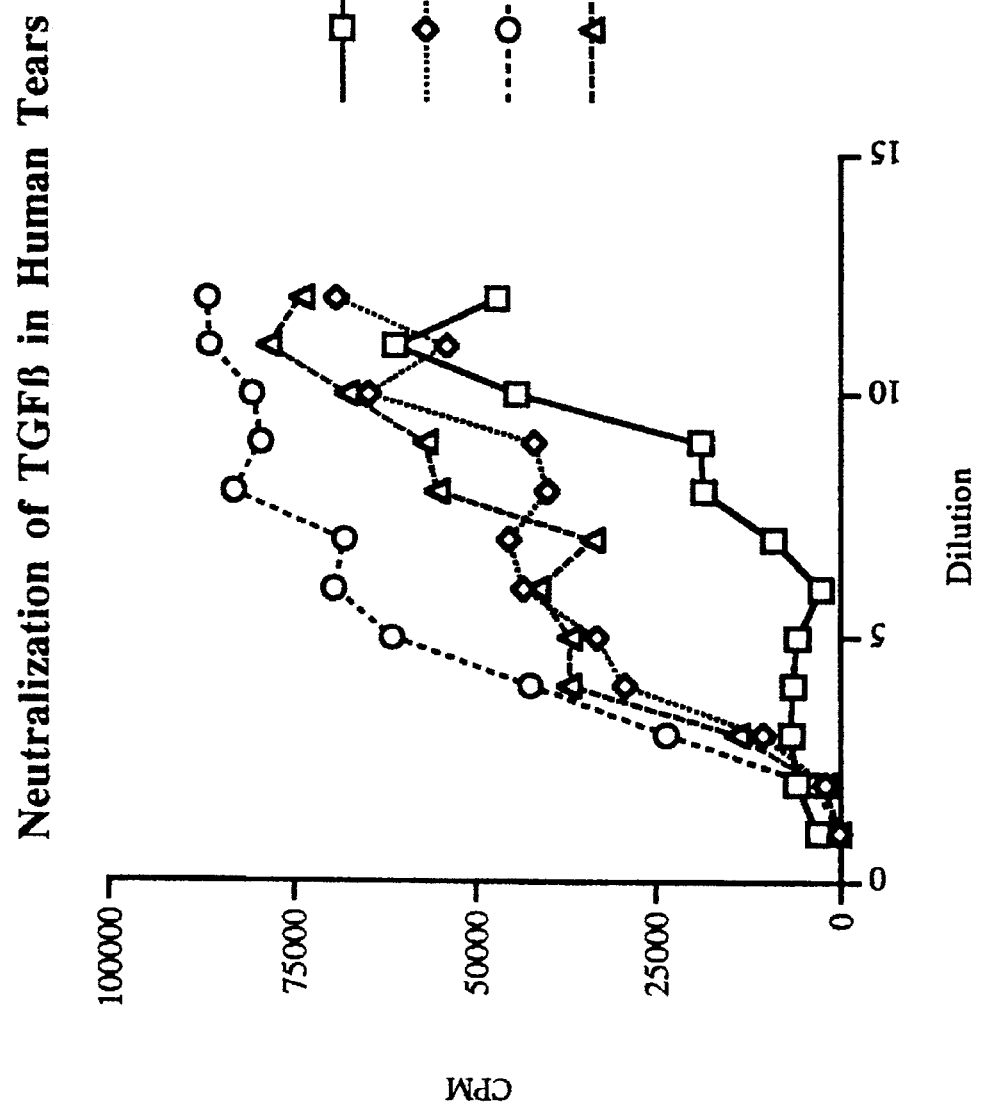
FIG. 7. Effect of TGFβ isotype specific neutralizing antisera on antiproliferative effects of human tears.
Figure 8:
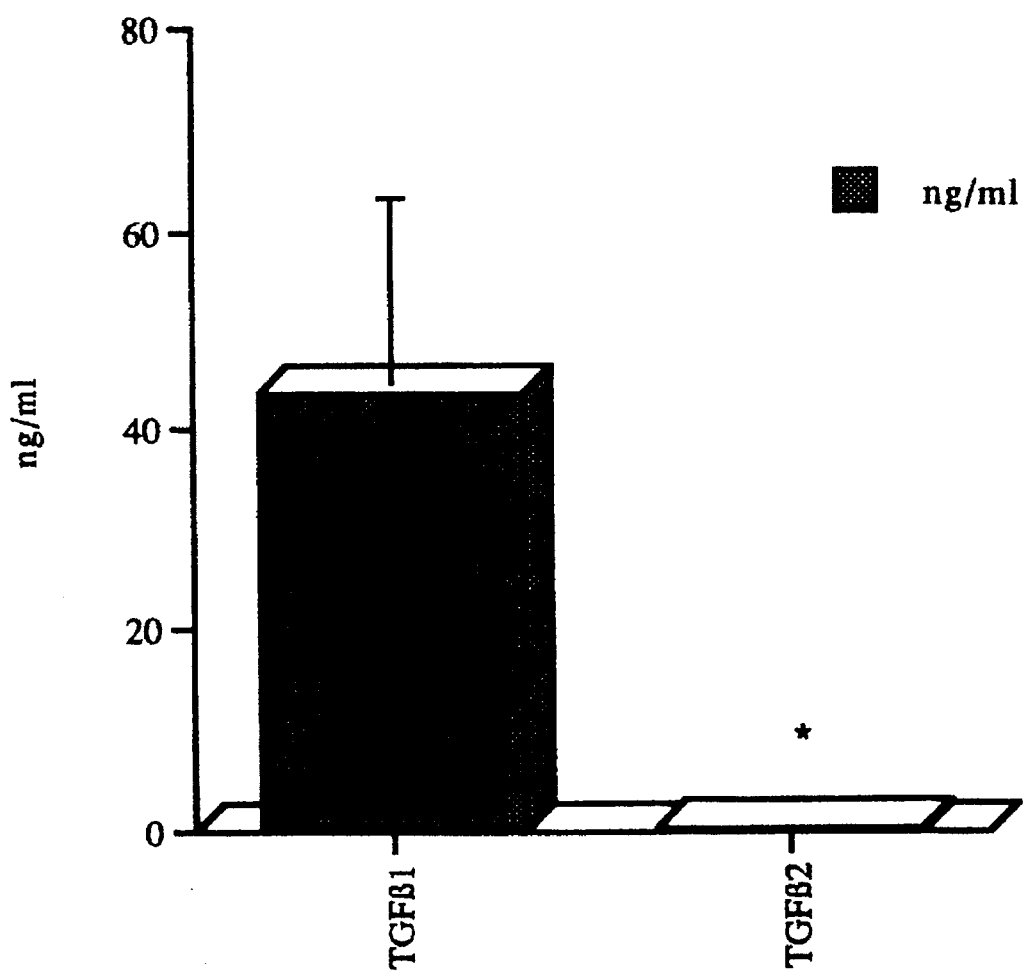
FIG. 8. Results of ELISA for TGF-β1 and TGF-β2 for human tears. TGF-β concentration in tears is 0.521 ng/ml+ 0.321. Tear TGF-β1 concentrations were significantly greater than TGF-β2 (P<0.05).

We recently evaluated human tears for TGFβ using the CCL-64 mink lung epithelial cell (MLEC) growth inhibition assay, a conventional assay for the detection of TGFβ, and sELISA (Danielpour D. et al. (1989) Cell Physiol. 138:79–86). Native human tears produced an anti-proliferative effect in the MLEC assay; however, a flat growth inhibition curve with rapid loss of anti proliferative activity after 3 to 7 serial dilutions was noted with native tears (FIG. 4). Heating and acidification, two physicochemical techniques previously reported to activate latent TGFβ increased the concentration of TGFβ in human tears calculated at the midpoint of the growth inhibition curves (FIG. 5). Furthermore, incubation of human tears with n-acetylcysteine ("MUCOCIL"™, DEY Laboratories, Napa, Calif.), a mucolytic and reducing agent, followed by heating at 80° C. for 8 minutes appeared to release latent TGFβ in tear samples, compared to tears treated by heating alone (FIG. 6). Following this treatment, a growth inhibition curve with a slow decay of the growth inhibition activity as tear specimens were serially diluted was obtained that resembled the curve obtained with serially diluted purified human platelet TGFβ1 (FIG. 6). The anti-proliferative effect of human tears in the MLEC assay could be inhibited by pre-incubation with TGFβ1 neutralizing anti-sera but not by TGFβ2-specific antisera (FIG. 7).

The presence of TGFβ in human tears was confirmed by TGFβ1 sELISA. TGFβ1 was not detected in native tear samples by sELISA; however, pre-treatment of human tears with n-acetylcysteine followed by heating resulted in an average detectable tear TGFβ1 concentrations of 45 ng/ml (range 19.99–67.7 ng/ml). TGFβ2 was detected in human tears by sELISA at very low concentrations (521 pg/ml with a range of 316–891 pg/ml) compared to TGFβ1 ($p<0.05$).

SDS-PAGE and immunoblotting experiments were performed to confirm the molecular weights (MW) of TFGβ complexes in human tears.

EXAMPLE 3

Western Blot Analysis

Western blots were preformed as follows. Kaleidoscope pre-stained molecular weight standard was purchased from Bio-Rad (Richmond, Calif.). Human platelet TGFβ1, rabbit anti-pan isotype TGFβ was purchased from R&D Systems, Inc. Anti-rabbit and anti-goat IgG-POD were purchased from Boehringer Mannheim (Indianapolis, Ind.).

Fresh human tear specimens were activated by the following methods: (1) heating at 80° C. for 7 minutes and immediately placed on ice; (2) diluted 1:1 with 10% N-acetylcysteine "MUCOCIL"™, DEY Laboratories, Napa, Calif.) then heated at 80° C. for 7 minutes and immediately placed on ice, (3) acidification by adjusting pH to 2 with 1N HCl and incubating at room temperature for 1 hour. The pH was then neutralized with one NaOH, (4) acidification, then reduction by addition of 5 ul of 1M dithiothreitol (DTT). All activated specimens were then added to 2× sample buffer and boiled at 100° C. for 3 minutes.

Mini-protein II 4–20% Ready gels were used for SDSpolyacrylamide gel electrophoresis (SDS-page) and were purchased from Bio-Rad. Running buffer contained Tris/glycine with SDS. Electrophoresis was performed at constant voltage (125 V) in a Bio-Rad mini-protein II electrophoresis cell until the dye marker had reached the bottom of the gel. Electrophoretic transfer on to PVDF membrane (Millipore, Beford, Mass.) was performed with a Bio-Rad Trans-Blot cell. Transfer buffer consisted of glycine/ethanolamine and 20% methanol. Prior to transfer, the PVDF membrane was pre-wet in 100% methanol, rinsed with distilled water and immersed for 15 minutes in buffer. Transfer was performed at 20 V overnight. After electroblotting, membranes were stained with Pouceu S (Sigma) for 2 minutes, then rinsed with water and air dried.

Figure 9:
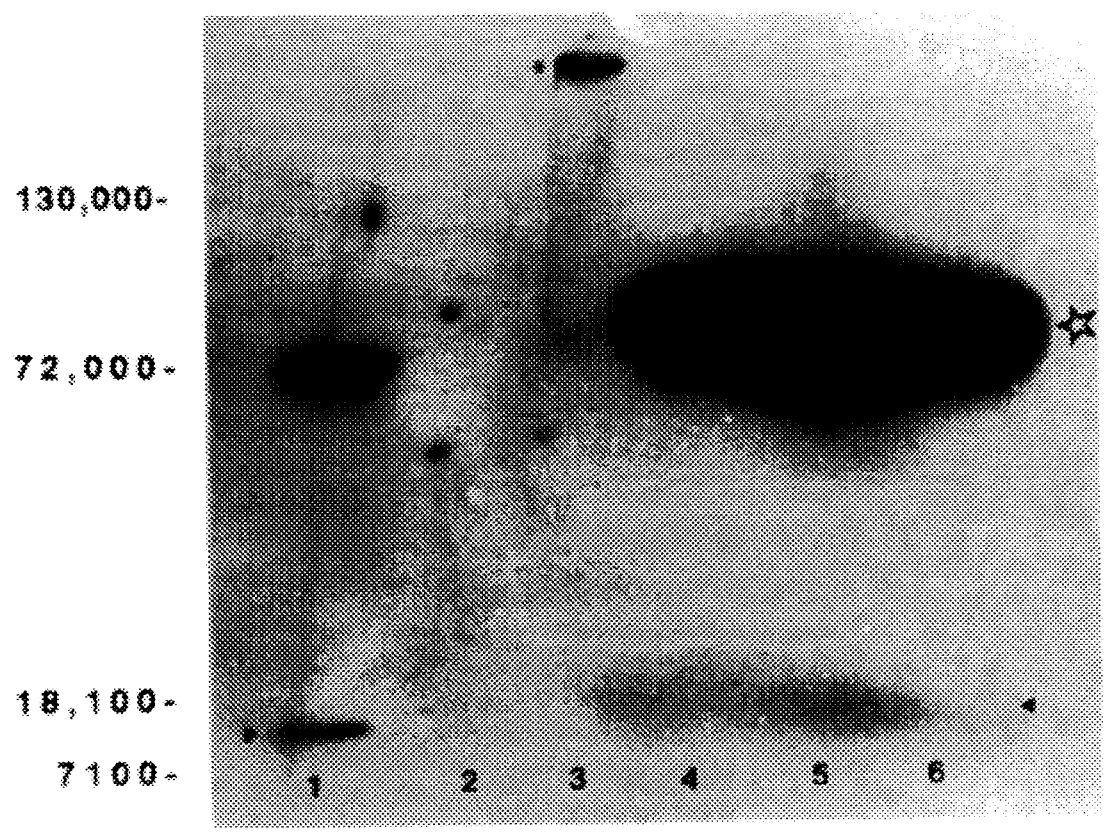
FIG. 9. Western blot of native tears treated with n-acetylcysteine and heating, showing pro-TGF-β binding to high MW complexes (about 1000 kD, probably mucins), and monomeric TGF-β. Lane 1 purified TGF-β1. (R&D), monomer band is present at approximately 12.5 kD (arrowhead); Lane 2. blank; Lane 3. native tears—a high molecular weight band (approximately 100 kD asterisk) is noted; lanes 4–6: tears treated with n-acetylcysteine and heating (lane 4), acidification with HCl (lane 5), and acidification followed by reduction with DTT (lane 6). Two bands of immunoreactivity were noted with these specimens, a stronger band at approximately 110 kD, the size of the pro-TGF-β complex (LAP plus cytokine, star) and a weaker band of the same size as monomeric TGF-β (approximately 12.5 kD. arrowhead)

Immunodetection was performed using a Bio-Rad chemiluminescent detection kit. The PVDF membrane was wet with 100% methanol, then rinsed with distilled water. The membrane was then incubated for 1 hour in blocking solution (1% blocking reagent in TBS) on a shaking incubator. The membrane was then incubated for one hour with primary antibody diluted in 0.5% blocking solution. Dilution of Pan-TGFβ antibody was 1:2000 (1 μg/μl). The membrane was then washed twice in TBST for 10 minutes each, then washed twice with 0.5% blocking solution. The membrane was then incubated for 1 hour with POD-conjugated secondary antibody diluted 1:1000 in 0.5% blocking solution. The membrane was then washed four times with TBST for 15 minutes each. Excess buffer was then drained from the washed membrane, and it was placed in a staining dish and incubated for 30 minutes at room temperature with a mixture of solutions A and B (diluted 1:100 and incubated for 30 minutes at room temperature prior to addition). Approximately 125 μl/cm sq. was added to the membrane container and incubated for 1 minute. The wet membrane was immediately placed into a plastic hybridization bag and the bubbles were removed. The membrane (protein side up) was placed into a film cassette against a sheet of X-ray film (X-Omat, Kodak, Rochester, N.Y.) and was exposed for 1 minute, then developed. Either no immunoreactive bands or high MW bands. (>50,000 kD) were observed in native or heat treated tears. Treatment of tears with n-acetylcysteine and heating, HCl, or HCl plus DTT resulted in immunoreactive bands at 110 kD, and 12.5 kD using TGFβ specific antisera (FIG. 9). These bands correspond to the published MWs of pro-TGFβ complexes and monomeric TGFβ.

Taken together, these results indicate than native human tears contain a small amount of biologically active TGFβ (approximately 3.8 ng/ml), and a greater amount of latent TGFβ that can be released by a variety of physiochemical techniques. TGFβ1 is the predominant isoform in tears. Our finding of TGFβ1 production by human lacrimal gland secretory acini coupled with the previously reported relative lack of immunoreactivity of human ocular surface epithelia for TGFβ (Pasquale, L. R. et al. Invest. Ophthalmol. Vis. Sci. 1993;94:23–30) (only superficial limbal epithelia were positive) suggests that some, if not the majority, of TGFβ in human tears may be produced by the lacrimal gland.

What is claimed is:

1. A method of ameliorating a tear deficiency condition comprising the steps of administering to the ocular surface a pharmaceutically effective amount of an ophthalmological composition comprising a pharmaceutically effective amount of TGFβ in a pharmaceutically acceptable carrier.

2. The method according to claim 1 for the tear deficiency condition is dry eye.

3. The method according to claim 2 wherein said dry eye disease is Sjogren's Syndrome.

4. The method according to claim 2 wherein the dry eye condition results from a condition selected from the group consisting of hyperproliferation, squamous metaplasia, loss of goblet cells, and abnormal terminal differentiation.

* * * * *